United States Patent [19]

Verbiscar

[11] Patent Number: 5,356,881
[45] Date of Patent: Oct. 18, 1994

[54] PLANT-DERIVED WILDLIFE REPELLENTS

[76] Inventor: Anthony J. Verbiscar, 491 Crestvale Dr., Sierra Madre, Calif. 91024

[21] Appl. No.: 952,062

[22] Filed: Sep. 28, 1992

[51] Int. Cl.$^5$ .................. A61K 31/705; A61K 31/56; A61K 31/35; A61K 31/34

[52] U.S. Cl. ........................ 514/26; 514/169; 514/451; 514/461; 514/918

[58] Field of Search ............ 424/195.1; 514/920, 514/461, 451, 169, 182, 26, 928

[56] References Cited

PUBLICATIONS

L. P. Brown, et al. Ann. N.Y. Acad. Sci., 443: 171–187, 1985.
D. L. Campbell, et al., Denver Wildlife Res. Center, USDA Olympia, Wash. 1991.
R. E. Marsh, Vertebrate Pest Management, pp. 253–285, from Adv. Urban Pest Mgmt., G. W. Bennett and J. M. Owens, Eds, Van Nostrand Reinhold, N.Y., 1986.

*Primary Examiner*—John W. Rollins

[57] ABSTRACT

Products from the plant species *Nerium oleander* and, *Urginea maritima*, are prepared and tested as wildlife repellents comparing them with digitalis products. Chemical compounds derived from these plants including oleandrin, oleandrigenin, scillirosidin, digitoxigenin and digoxigenin are shown to cause nausea and emesis at low doses in pigeons and to repel, mice, rats, gophers, meadow voles and mountain beavers. After ingestion these animals quickly learn to avoid targets treated with the plant-derived repellents. When the remembrance of a treated food or other target lasts for an extended period of time it can be termed an aversion conditioning agent. Such products can be used for the protection of other plants, seeds, buildings, structures, communication cables and animals exposed to wildlife.

10 Claims, 1 Drawing Sheet

OLEANDRIN     R = OLEANDROSE

OLEANDRIGENIN   R = H

SCILLIROSIDIN

Figure 1:
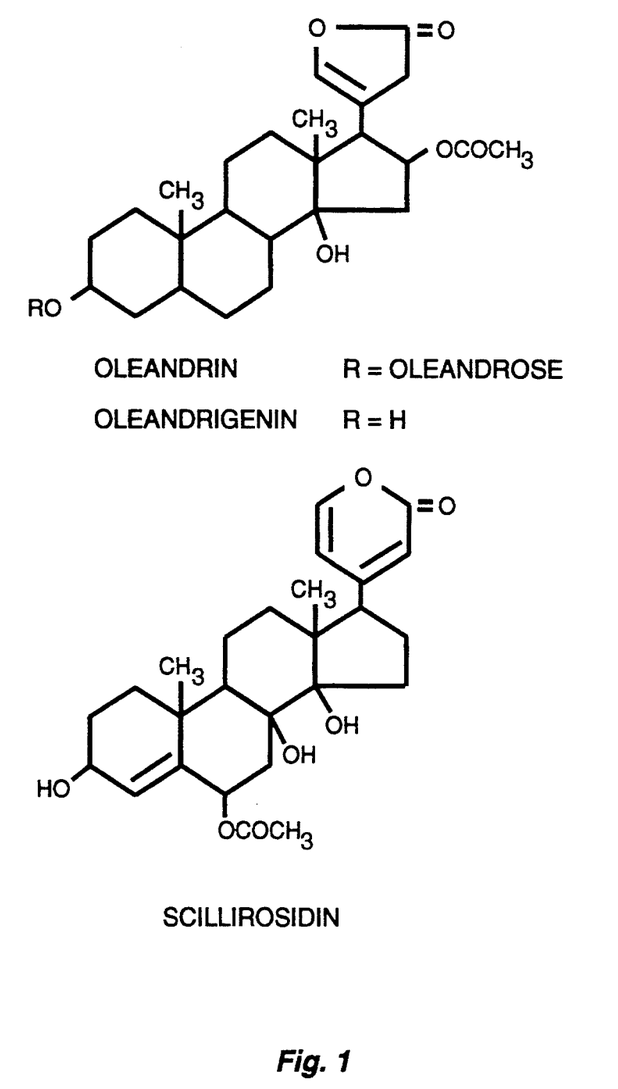

*Fig. 1*

PLANT-DERIVED WILDLIFE REPELLENTS

STATEMENT OF RIGHTS

This invention was made with support from the National Science Foundation under grant number ISI-8713502. The United States Government has certain limited rights to this invention.

FIELD OF INVENTION

This invention concerns various products of oleander, and red squill as emetic animal repellents.

BACKGROUND OF INVENTION

Wildlife are a serious economic problem in certain agricultural, industrial, commercial and urban environments. Deer, moose, and elk browse on tree seedlings planted by foresters (Black, 1992), and Feed on a variety of ornamental plants. Beaver cut trees and flood out others. Coyotes and wolves kill grazing sheep (Gaafar et al., 1985). Rabbits and hares are a constant problem in newly planted fields and reforested areas. Gophers chew through underground communications cables requiring extensive searches for the damaged section and subsequently expensive repairs. Birds feed on seed sown for agricultural purposes. Pigeons deface commercial properties. There is a continuing need to control these wild species because of the extensive economical damage they cause (Marsh 1986, 1988, 1990). Products which when ingested by wildlife cause nausea, agitation, malaise and gastrointestinal illness are potential aversion conditioning agents. The effect must be fast so that the animal associates the feeling with the ingested target item and this association must be long lasting, i.e. remembered and related to the target.

Wildlife naturally learn to avoid certain plants for reasons which include taste, odor and illness. Plant-derived products are especially attractive as wildlife repellent agents because they are already in the environment, protecting these species against predators. Natural products which have been investigated as animal repellents include bitter quinine, hot tasting capsaicin from peppers, bone tar oil and putrescent whole egg solids. Other plant derived products considered as potential animal repellents include simmondsin in jojoba seeds, strychnine, red squill powders and digitalis glycosides. Digitalis extracts were originally bioassayed in pigeons for emesis as an estimate of potency. The digitalis glycosides cause nausea and vomiting as a side effect to their normal cardiotonic activity. *Digitalis lanata* and *D. purpurea* are cultivated in the Netherlands. Red Squill, *Urginea maritima*, contains the toxic and emetic glycoside scilliroside. Scilliroside and other red squill preparations have been registered in the United States as rodenticicles, but supplies of this slow growing Mediterranean region bulb plant are limited. Scilliroside emesis occurs at lower doses than its lethality in humans and other animal species, thereby serving as a safety factor.

*Nerium oleander* is an evergreen plant that is indigenous to the Mediterranean region, sub-tropical Asia, and India. It is now ubiquitous California, Arizona, Florida, and other warmer climate states. It is a common ornamental plant used in urban gardens, along highways, golf courses and other municipal facility landscapes. The plant grows well with minimal water and is universally avoided by wildlife, probably because of its emetic activity. In Asia oleander is considered a therapeutic plant used for treating swelling, leprosy, eye and skin disorders. The leaves also possess diuretic and cardiotonic properties, principally due to the presence of oleandrin, a digitalis-like glycoside. Oleandrin occurs in leaves, stems, floral parts and resin. Oleander also contains oleandrin related glucoside conjugates. Oleandrin itself and these glucosides yield the aglycone oleandrigenin on acid hydrolysis. The glycoside conjugate of oleandrin is oleandrose. The active components of oleandrin and oleandrigenin are tasteless, odorless and highly emetic.

The digitalis-derived aglycones gitoxigenin, digitoxigenin and digoxigenin have similar structures. Scillirosidin, oleandrin and oleandrigenin differ from the digitalis aglycones in that they contain acetoxy groups which increases their activity. It is important that there is a dose differential between the toxic and emetic activity in these plant derived products. The products will all degrade in the environment due to hydrolysis of their acetoxy and lactone groups, rendering them inactive.

SUMMARY OF INVENTION

This invention pertains to various products from oleander (*Nerium oleander*), and red squill (*Urginea maritima*) for use as wildlife repellents. Preparations from these plants cause animals to avoid the treated target, because of toxicosis or nausea which result from ingestion of the product. The various products cause emesis in some animal species, and sickness in others which are unable to vomit. Most of the products prepared and tested are aglycones of natural plant glycosides. These include scillirosidin from scilliroside (red squill), digitoxigenin, digoxigenin and gitoxigenin from digitoxin, digoxin and gitoxin (digitalis) respectively, and oleandrigenin from oleandrin (oleander). These glycosides are all known to be emetic, but we found the glycan moiety is an unnecessary appendage for emesis. The aglycones generally act faster as emetics following oral ingestion, because they will absorb better than the parent glycosides from the gastrointestinal system into the circulation, and thence into the brain. A chemoreceptive trigger zone in the brain has been demonstrated where the digitalis-like products exert an action resulting in emesis (Wang, 1965). The water soluble digitalis glycosides probably do not pass the blood-brain-barrier unless they are enzymatically hydrolyzed in their lipid soluble aglycones. The lipid solubility of oleandrin and oleandrigenin are similar, and show a similar emetic activity.

The acute oral toxicity and repellency of 998 chemicals to one or more of 68 wild and domestic birds was determined (Schafer et al., 1983). Arian repellency and toxicity did not correlate as repellency varied independently of toxicity. Many natural products from plants were included in this study. The data presented in a later review (Riley and Tuck, 1985). where several hundred chemicals were referenced, demonstrated further that there are many toxins which do not ellicite an aversion reaction. An example of a toxic substance that is ineffective as an aversion conditioner is sodium cyanide (Nachman and Hartley, 1975).

Scilliroside lethality and emesis are well documented. The differential between the toxic and emetic doses of scilliroside for humans (Belt, 1944), cats and dogs (Gold et al., 1950) is known. A differential between a lethal and an emetic or sickening dose is necessary for use as a wildlife aversion conditioning product. Scilliroside and scillirosidin are extremely lethal to rats and mice (Rothlin and Schalch, 1952; Verbiscar et. al., 1986). These and other rodents are unable to vomit and eliminate residual toxic products from their stomachs. Scillirosidin emesis is demonstrated here for tile first time, Table 1, tests 17, 18 and 19 (Marsh et al., 1985). Emesis occurs in pigeons at 0.01% levels in feed. At 0.01% scillirosidin level, rats learn to avoid treated feed, probably because of illness or malaise, Table 2, tests 24 and 25. Lethality of scillirosidin occurs at lower doses in female rats than it does in males, Table 2, tests 26, 27 and 28 (Verbiscar et al., 1987). The role of illness in a learned aversion to red squill powder baits has been reported (Nachman and Hartley, 1975). The use of scillirosidin preparations for the purpose of repelling wildlife is new.

Digitoxin has been evaluated as an aversion conditioning agent for raccoons (Conover, 1989). Blue jays were repelled by pigeon feed treated with digitoxin, digoxin and digitoxigenin (Brower and Fink, 1985). When a large enough dose was ingested the blue jays regurgitated. In Table 1, test 1 digitoxigenin is seen to have only a minimal effect in pigeon feed at a 0.03% level, causing only one of six pigeons to retch or vomit. In tests 5 and 8, digoxigenin is seen to be slightly more active where four of eleven pigeons retched or vomited at a 0.03% level in the feed. Although some pigeons exhibited a head shaking reaction for gitoxigenin, none retched or vomited, test 4. The absence of emetic activity in gitoxigenin, also termed desacetyloleandrigenin, parallels the low toxicity of desacetylscillirosidin in rats (Verbiscar et al., 1986, 1987). The acetoxy groups of oleandrigenin and scillirosidin apparently enhance activity. Oleandrin and scillirosidin at lower closes are more emetic than the digitalis aglycones tested here.

TABLE 1

Emesis of Plant Derived Products in Pigeons

| Test | Product | Active product, % | Avg. product ingested, mg/kg | No. Pigeons Total | No. Pigeons Retch or vomit |
|---|---|---|---|---|---|
| 1 | Digitoxigenin | 0.03 | 0.72 | 6[a] | 1 |
| 2 | Oleandrigenin | 0.03 | 1.61 | 6 | 5 |
| 3 | Oleandrin | 0.03 | 2.94 | 6 | 6 |
| 4 | Gitoxigenin | 0.03 | 1.83 | 6[a] | 0 |
| 5 | Digoxigenin | 0.03 | 2.49 | 6[a] | 1 |
| 6 | Oleandrin | 0.03 | 0.97 | 6[b] | 2 |
| 7 | Oleandrin | 0.01 | 0.28 | 6[b] | 3 |
| 8 | Digoxigenin | 0.03 | 0.74 | 5 | 3 |
| 9 | Oleander Extract | 0.015 | 0.32 | 6[b] | 2 |
| 10 | Oleander Extract | 0.02 | 0.14 | 3[b] | 1 |
| 11 | Oleander Extract | 0.02 | 3.03 | 6 | 6 |
| 12 | Oleandrin | 0.01 | 1.55 | 6 | 6 |
| 13 | Oleandrin | 0.005 | 1.02 | 3 | 3 |
| 14 | Oleandrin | 0.01 | 0.11 | 3[c] | 3 |
| 15 | Oleandrin | 0.005 | 0.0 | 3[d] | 2 |
| 16 | Oleandrin | 0.005 | 0.01 | 3[e] | 2 |
| 17 | Scillirosidin | 0.01 | 0.14[g] | 3 | 2 |
| 18 | Scillirosidin | 0.03 | — | 3 | 3 |
| 19 | Scillirosidin | 0.05 | 0.37[g] | 6[b,f] | 6 |

[a]Several pigeons demonstrated a head shaking reaction
[b]Several pigeons ate little or no bait
[c]Reexposure of test 12 pigeons 28 days later
[d]Reexposure of test 13 pigeons 22 days later
[e]Reexposure of test 15 pigeons 77 days later
[f]Reexposure of test 17 and 18 pigeons 8 days later
[g]Approximate due to mixture of vomitus with bait

TABLE 2

Effect of Scillirosidin[a] in Rat Feed

| Test | Active product % | Avg. rat weight, g | Avg. bait ingested, g | Avg. product ingested mg/kg | Mortality/ test animals |
|---|---|---|---|---|---|
| 24 | 0.01 | 208 | 1.4 | 0.68 | 0/6 |
| 25 | 0.01 | 208 | 2.4 | 1.14 | 0/6 |
| 26 | 0.03 | 204 | 1.4 | 1.98 | 3/6[b] |
| 27 | 0.03 | 235 | 1.3 | 1.65 | 3/6[c] |
| 28 | 0.05 | 213 | 1.2 | 2.6 | 2/6[d] |

[a]A technical scillirosidin containing 67% active product
[b]Only female rats died consuming 1.85 mg/kg compared to males at 2.11 mg/kg
[c]Only female rats died consuming 1.81 mg/kg compared to males at 1.48 mg/kg
[d]Only female rats died consuming 2.60 mg/kg compared to males at 2.95 mg/kg

*Nerium oleander* leaves, twigs, sap (resin) and flowers contain oleandrin and related glycosides, which protect the plant against wildlife predators. The plant is evergreen and grows extensively throughout urban environments in Southwestern United States and in other warm areas. Oleander leaves have been used to control insects and rodents (Secoy and Smith, 1983). The toxicity of oleander and oleandrin is known for humans (Shaw and Pearn, 1979), cattle, sheep, hens, ducks, geese, cats, dogs (Szabuniewicz et al., 1971) and monkeys (Schwartz et al., 1974). The principal early signs of oleander toxicity in humans, dogs, cats and monkeys is salivation, nausea and vomiting. The lethal dose of oleandrin varies substantialy among different species. Emetic doses were never measured per se independently of lethal doses. Surviving animals do vomit indicating that emesis occurs at lower doses than mortality. This was found to be the case here for pigeons, Tables 1. and 3. Other animals including mice, rats, gophers, meadow voles and mountain beaver were repelled by treated feeds before ingesting lethal doses. These birds and animals learned to avoid the treated feeds which they normally eat (Marsh and Verbiscar, 1991).

In Table 1 it is seen that oleander products including oleandrin, oleandrigin and purified oleander extract had the highest emetic activity at the lowest doses. There was little or no difference between oleandrin and oleandrigenin as emetics in pigeons, indicating similar absorbtion and distribution to emetic trigger receptors. Oleander emesis is relatively fast and generally occurred when the pigeons consumed about 0.3 mg/kg or more. In test 3 one pigeon death occurred at 4.9 mg/kg, and a second one at 1.5 mg/kg, on the day following the tests. These were the only two pigeons to die. Levels as low as 0.005% oleandrin in pigeon feed caused emesis, test 13, 15 and 16. Test 10 with oleander extract did not produce as good an emetic action as test 11 because pigeons in test 10 were less hungry, having fasted for 28 hours compared to 48 hours for all other pigeon tests. The pigeons used in tests 10-16, were naive and not used previously in any test. A summary of results for test 11, Table 3, are typical of these pigeon experiments.

TABLE 3

Test 11
Chemical Oleander glycoside extract (R93-1) % Active ingredient: 0.02%

| Pigeon | Wt. in grams | Treated diet (grams) | | | | Mg/kg chemical consumed | Comments |
|---|---|---|---|---|---|---|---|
| | | Amount offered | Amount left | Amount consumed | Amount regurgitated | | |
| 1 | 497 | 15.0 | 5.3 | 9.7 | 9.0 | 3.90 | Consumed a good amount of grain. Retched at 15 min into the test and vomited at 17 minutes. This was repeated over the next 30 min. |
| 2 | 678 | 15.0 | 8.3 | 6.7 | 5.2 | 1.98 | Consumed considerable grain and began retching at 21 min. Vomited at 22 min. This was repeated several times during the remaining portion of the test. |
| 3 | 592 | 15.0 | 5.9 | 9.1 | 8.6 | 3.07 | Consumed substantial amount of grain. Retched at 10 min into test but did not vomit until 32 min into test. Retching and vomiting were repeated a number of times. |
| 4 | 609 | 15.0 | 6.9 | 8.1 | 8.1 | 2.66 | Consumed substantial grain and retched at 19 min into test. Spent most of hour doing nothing. Did not vomit during 1-hr test but vomited extensively sometime during next 2 hrs. |
| 5 | 586 | 15.0 | 5.2 | 9.8 | 9.3 | 3.34 | Consumed a good amount of grain and exhibited a lot of head shaking. Did not retch or vomit during 1-hr test period. Vomited extensively sometime during next 2 hrs. |
| 6 | 578 | 15.0 | 5.7 | 9.3 | 8.1 | 3.22 | Consumed a good amount of grain and exhibited a lot of head shaking and feather ruffling. Retched and vomited at 30 min into test. This was repeated several times during test. Some additional vomiting occurred during next 2 hrs. |

Remarks:
All 6 pigeons consumed substantial amounts of grain. Bird numbers 1 and 2 did not vomit during the 1-hour test but did vomit during a 2-hour period that followed. All birds that retched and vomited during the 1-hour test period did so repeatedly with relatively intense reactions. Oleander glycoside extract at this concentration produced a strong emetic action in all pigeons. These pigeons had never been used for any previous tests.

It was noted in earlier tests here as they progressed chronologically in time that some pigeons became less responsive to feeding on the treated cracked corn diets. Some of the original group of 30 pigeons were tested a second or third time, as they were randomly removed from a common cage. Test pigeons were always given a minimum rest period of at least three weeks. Nevertheless, they were less apt to feed on chemically treated cracked corn diets on subsequent exposure, even when a different emetic was used. The oleander derived products were principally responsible because they produced the strongest emetic reaction.

The aversion conditioning action of oleandrin was clearly demonstrated in tests 12-16. In test 12 six naive pigeons were offered a 0.01% oleandrin diet. The pigeons consumed a moderate amount of diet with a mean consumption of 8.6 grams containing 1.55 mg/kg oleandrin. All six pigeons retched and vomited, five within 13 to 21 minutes following the start of feeding. Twenty eight days later three of the six pigeons in test 12 were retested in test 14. Although consumption of feed was very low at a mean of 0.63 grams per pigeon, two pigeons vomited. The third pigeon retched having eaten only 0.1 gram of the treated cracked corn.

In test 13, this experiment was repeated with three naive pigeons at a 0.005% level of oleandrin in the diet. All three pigeons ate substantial amounts of the cracked corn diet and regurgitated the feed within 28 to 45 minutes. When these same three pigeons were reexposed to the same 0.005% oleandrin diet 22 days later, none of the three would even taste treated cracked corn, test 15. Even so, two of the pigeons retched immediately after exposure to the diet. When removed from the test and given their normal pigeon feed which contained no cracked corn, they eagerly ate 24.2, 29.8 and 45.0 grams each during a 1 hour period. This illustrated they were not conditioned to avoid all feed.

In test 16, the same three pigeons were tested a third time, 77 days after test 15, and 99 days after the initial test 13. Two pigeons retched before even tasting the grain, and one of these vomited after tasting only a few particles. Following this one hour test and another one hour waiting period, each of these pigeons was offered a bowl of untreated cracked corn and a bowl of pigeon mix with no cracked corn content. Less than 0.5 grams of clean cracked corn was consumed by any bird but substantial amounts of pigeon mix, 25.1, 14.6 and 32.6 grams, were consumed in one hour of feeding. This clearly indicates a strong aversion to cracked corn, whether or not it is treated with oleandrin.

In test 20, five wild house mice were offered coarse cracked corn containing 0.03% oleandrin. Mean 20 hour consumption was 0.38 grams, or 5.56 mg/kg of oleandrin. The low bait intake indicates a rapid physiological reaction greatly reducing normal feed consumption. The mice avoided eating the treated feed.

In test 21, ten Swiss Webster laboratory mice were offered an EPA-type diet containing 0.3% oleandrin. Mean 20 hour consumption was 0.12 grams, or 14.5 mg/kg of oleandrin. One mouse died having consumed four times the average. Control mice ate a mean of 5.9 grams of this diet. The mice offered the treated diet ate only 2% of the controls as they quickly learned to avoid the treated feed.

In test 22, six Sprague-Dawley rats were offered the 0.3% oleandrin content EPA-type diet. Mean 20 hour diet comsumption was 2.1 grams, or 35.4 mg/kg of oleandrin. A control group ate an average of 14.8 grams of the placebo diet. The rats quickly learned to avoid this high level activity feed.

In test 23, six Sprague-Dawley rats were given a free choice placebo EPA-type diet and one containing only 0.02% oleandrin in an oleander extract. Mean 20 hour treated diet consumption was 6.3 grams, or 2.4 mg/kg of oleandrin, in a range of 1.0 to 13.4 mg/kg. No mortality occurred.

In test 29, Example 9, six pocket gophers, *Thomomys bottae*, were offered a crimped oat diet containing 0.3% oleandrin in a one day no-choice test. Mean intake of this high dose level feed was 20.6 mg/kg. Three go- 
phers died within three days, suggesting this as a potential rodenticide for gopher control.

In test 30, Example 10, six meadow voles, *Microtus californicus*, were offered a crimped oat diet containing 0.3% oleandrin in a one day no-choice test. Diet consumption was low with a mean intake of oleandrin at 38.9 mg/kg. There were no deaths. Oleandrin is less toxic to meadow voles than it is to gophers. Meadow voles also learned to avoid oleandrin treated diet readily, whereas several gophers ingested lethal doses of the same treated diet.

A test was made to evaluate the effects of oleander extract on mountain beaver, *Aplodontia rufa* (Campbell et al., personal communication, 1991). Two adult animals were exposed to treated and untreated sword fern fronds in an outdoor pen with burrows. The treated fronds were sprayed with a 0.5% suspension of oleander extract containing 16% oleandrin (0.008%) and 5% Roplex AC-33 adhesive. The oleander extract caused a sharp reduction in acceptance of sword fronds from 65% to 0% in two exposure periods of four test days each. The mountain beavers remained active at the end of the tests.

Neutral hydrophilic adherent aids such as methylcellulose, hydroxyethylcellulose and hydroxypropylcellulose which are non-toxic, harmless to the plants, other targets and the environment, and will not facilitate deactivating hydrolysis of the acetoxy and lactone functions of the emetic agents, can be formulated with the agents in water to effectively bind the agents to the targets by spraying, brushing, dipping or other application. As an example of a potential use, more than 3 million acres of commercial tree seedlings are planted each year in the United States, where browsing by mountain beaver, deer, elk and other wildlife is substantial. Oleander preparations especially can protect nurseries and reforested areas from destructive wildlife.

BRIEF DESCRIPTION OF THE DRAWING

FIG. 1 presents chemical structures of highly emetic plant-derived wildlife repellents.

EXAMPLES

EXAMPLE 1

*Nerium Oleander* Leaf Extract

Fresh oleander leaves were dried overnight in a forced air oven at 65° C. The leaves were ground to a fine flour in a hammer mill. A 500 gram quantity of this green leaf flour meal was extracted with 1 liter of isopropyl alcohol in a Waring blendor for one hour at room temperature. The leaf meal was filtered then reextracted with a second 1 liter of isopropyl alcohol in the Waring blendor for 1 hour. After filtration the dark green extracts were combined and treated with 200 ml of 5% aqueous lead acetate with stirring for five hours to precipitate phenolics as lead salts. The precipitate was filtered and the dark green filtrate was taken to dryness under vacuum on a rotary evaporator. The dark green oily residue was mulled in 1 liter of hexane as product solidified to 45.5 grams of green powder. This product was sequentially extracted with 400 ml methylene chloride, followed by 300 ml methyl alcohol. On stripping the methylene chloride extract to dryness there resulted 16.4 grams of dark green crystalline product containing 15% oleandrin. The evaporated methanol extract yielded 10.6 grams of greenish yellow crystalline product containing 5% oleandrin. This represents a recovery of 2.99 grams oleandrin from 500 grams dry leaves, or about 0.6% yield. The hexane mull also contained some oleandrin. The solid extracts were bitter.

The two solid products were combined and extracted into 400 ml of methylene chloride. This solution was washed with 2×100 ml 0.2N hydrochloric acid, followed by 2×100 ml 5% sodium bicarbonate solution. The methylene chloride solution was then passed through a column 2.5×40 containing 50 grams of silica gel 0.05–0.5 mm, washing with another 300 ml of methylene chloride. Most of the oleandrin and other glycosides were retained on the column. They were washed off the column with 300 ml of methylene chloride:methanol. On evaporation to dryness this eluant yielded 3.95 grams of non-bitter greenish powder containing 50% oleandrin.

Thin layer chromatography was run on silica gel 60 G plates using (9:1) ethyl acetate:hexane developer for a distance of 15 cm (system A). The plates were sprayed with 10% sulfuric acid, warmed gently on a hot plate, and viewed under long wave length ultraviolet light (UVL). The original leaf extract contained six blue fluorescent spots which indicates the presence of a lactone ring, including $R_f$ 0.63 (oleandrin), 0.53 (oleandrigenin), 0.42, 0.23 (gitoxigenin), 0.15 and 0.03. The acid-base washed and column processed product silowed only the five faster spots. The major blue fluorescing component in each product is oleandrin, The $R_f$ 0.42 spot is probably desacetyloleandrin. The $R_f$ 0.15 and 0.03 spots are probably di- or triglycosides of oleandrin related compounds. Using (95:5) acetonitrile:water developer (system B), oleandrin $R_f$0.83 did not separate as well from oleandrigenin $R_f$0.80.

Oleandrin was quantitated using high pressure liquid chromatography (HPLC), composed of a precolumn 3.2×40 mm of Porasil A 37–75 microns, a column 3.2×500 mm of silica gel 5 microns, (97:3) acetonitrile:-water eluant at 0.5 ml/min., detecting at 240 nm (system C). In this system the retention times were oleandrin 11.1 min. and oleandrigenin 12.1 min. Gitoxigenin (desacetyloleandrigenin) elutes at about 14 minutes in this system.

EXAMPLE 2

*Nerium Oleander* Twig Extract

Fresh deleafed twigs of oleander were dried overnight in a forced air oven at 65° C. The twigs were then ground to a flour in a hammer mill. A 300 g portion of this dry twig meal flour was extracted in a Waring blendor with 2×500 ml of acetone for 20 minutes each. The combined filtrates were treated with 50 ml of 5% aqueous lead acetate to precipitate phenolic lead salts. After good stirring and overnight standing the precipitate was filtered, and the acetone solvent was taken to dryness on a rotary evaporator under vacuum. The residue was extracted into methylene chloride, filtered free of insolubles, then stripped to dryness. After mulling in a small amount of acetone there resulted 5.56 grams of a dark green powder. The product was assayed by HPLC in system C, resulting in 44% oleandrin, representing a 0.8% yield in the dry twigs. The HPLC peak patterns of the leaf and twig extract products were similar. However, the twig extract product was only slightly bitter.

EXAMPLE 3

Preparation of Oleandrigenin

A solution of 4.0 grams of oleandrin in 200 ml of methanol and 50 ml of 0.1N hydrochloric acid was refluxed for 2.5 hours. After this time a TLC monitor indicated that hydrolysis of the oleandrose from oleandrin was complete. The solution was neutralized with sodium hydroxide, then taken to dryness under vacuum on a rotary evaporator. The residue was extracted into ethyl acetate, washed with water, then dried over anhy. sodium sulfate. A semi-solid mass resulted on evaporation of the solvent. The mass was recrystallized from hot dimethoxypropane to yield 2.54 grams of white crystalline product composed of 85% oleandrigenin plus about 15% gitoxigenin (desacetyloleandrigenin). A higher purity product was obtained by recrystallization from ethyl acetate:hexane (1:1). HPLC in system C gave retention times for oleandrigenin 12.0 minutes and gitoxigenin 13.9 minutes. TLC in system B gave blue Fluorescent spots for oleandrigenin $R_f$ 0.80 and gitoxigenin $R_f$ 0.69. An infrared spectrum in chloroform showed absorption peaks in $cm^{-1}$ at 3490(OH free), 3350(OH bonded), 2920 and 2860(CH), 1770(lactone), 1732(acetoxy), 1627 and 1613 (C=C), 1375(CH$_3$) and 1180 (C—O), consistent with the structure for oleandrigenin.

EXAMPLE 4

Preparation of Gitoxigenin

A suspension of 4.7 grams of gitoxin in 300 ml of ethanol containing 4.7 ml of conc. hydrochloric acid was stirred for three days, warmed gently for ten hours then stirred for another day at room temperature. The acidic solution was neutralized by the addition of solid sodium carbonate, then filtered to yield a clear colorless solution. The solvent was removed on a rotary evaporator and the residue was mulled in water to remove carbohydrate hydrolysis products. The residue was extracted into a solution of 100 ml of ethyl acetate and 30 ml of acetone, then filtered. A product crystallized as the solvent was removed under vacuum. The residue was mulled in ethyl ether to yield 2.2 grams of white crystalline gitoxigenin. On HPLC using system C as in Example 1. gitoxigenin had a retention time of 13.9 minutes, compared to a starting material reference gitoxin at 20.7 minutes. On TLC using system B gitoxigenin showed a blue fluorescent spot at $R_f$ 0.69, compared to gitoxin at $R_f$ 0.23. The product was about 95% pure gitoxigenin.

EXAMPLE 5

Preparation of Digitoxigenin

A solution of 6.0 grams of digitoxin in 300 ml of 95% aqueous ethanol containing 6.0 ml of conc. hydrochloric acid was stirred at room temperature with a bar magnet system. The hydrolysis was monitored by HPLC and TLC. At 20 hours digitoxin no longer appeared as an intact compound, and several intermediates were present. After 35 hours stirring all three digitoxose units had been removed, and there was no change in the hydrolytic products after another 60 hours. After hydrolysis to aglycone was complete, 7 grams of sodium carbonate was added to neutralize the solution. The solvent was evaporated to near dryness under vacuum on a rotary evaporator. On addition of 25 ml of water an oil separated and crystallized on standing. The product was dissolved in 75 ml of methylene chloride, which was washed with water to remove digitoxose. The solution was evaporated to dryness under vacuum leaving a glassy residue. This was dissolved in ethyl ether whereupon crystallization began immediately. After overnight refrigeration the digitoxigenin product was collected as 2.13 grams of white crystals, m.p. 240°–245°, homogeneous on TLC. The ethyl ether mother liquor contained additional digitoxigenin plus unidentified carbohydrate. Isopropyl ether was used to crystallize additional digitoxigenin from its digitoxose hydrolysis products. On TLC using system B the $R_f$ values were digitoxigenin 0.80 and digitoxin 0.63, both blue fluorescing. On HPLC in system C, Example 1., the retention times were digitoxigenin 11 minutes, and digitoxin 16 minutes.

EXAMPLE 6

Preparation of Digoxigenin

A suspension of 4.7 grams of digoxin in 300 ml of 95% aqueous ethanol containing 4.7 ml of conc. hydrochloric acid was stirred for four days with a bar magnet stirrer at ambient temperature. Crystalline sodium carbonate was added to neutralize the solution. The filtered solution was evaporated to dryness under vacuum resulting in a white semi-solid residue. This was mulled well in 50 ml of water to remove carbohydrates. The air dried product was dissolved in acetone, filtered and the solution was evaporated to dryness. The product was mulled in ethyl ether to yield 2.4 grams of white crystalline digoxigenin hydrate, m.p. 130°–140°. On HPLC in system C the product was homogeneous with a retention time of 15.2 compared with 20.7 min. for digoxin. TLC in system B gave a blue fluorescent spot at $R_f$ 0.64 for digitoxigenin, compared with $R_f$ 0.49 for digoxin.

EXAMPLE 7

Pigeon Testing

Test Method

The powder or crystalline compound was dissolved in alcohol, then coarse cracked yellow corn was added to the container. The corn was stirred vigorously so that it was completely wetted with the alcohol solution of the product. The treated wet corn was then dried in trays overnight at room temperature. Emesis testing was carried out with domestic pigeons (*Columba livia*). Three pigeons were tested at a time in individual plexiglass aquarium test chambers with wire mesh tops. Each chamber contained two bowls, one containing water and the other pigeon feed. The pigeons were removed from their large cage where they were collectively housed and placed in the test chamber 4 days prior to the actual test. Food and water were provided ad lib for the first 2 days. For the next 2 days the pigeons were deprived of food so that they would be hungry and immediately begin to feed when offered the treated test diet. After exposure to the treated diet the pigeons were observed closely for 1 hour and then for as long as 3 hours. Behavioral activities were recorded including eating, retching, vomiting, neck stretching and head shaking. Feed intake, dried vomitus and pigeon weights were taken. The time of initial retching and vomiting was noted. Tests are summarized in Table 1.

Digitoxigenin Results

In test 1, six fresh pigeons with an average weight of 666 grams were offered 0.03% digitoxigenin treated cracked corn feed. Four of the six pigeons consumed the grain, two of these in fair amounts of 2.5 and 3.1 grams. Only the pigeon consuming 3.1 grams retched and vomited at about 30 minutes following start of feeding. Four pigeons taking 0.7 to 2.5 grams demonstrated head shaking. The sixth pigeon ate only 0.1 gram and did not react.

Digoxigenin Result

In test 5, six pigeons with an average weight of 669 grams were offered 0.03% digoxigenin treated cracked corn diets. Five of the pigeons consumed an average of 6.7 grams of feed and demonstrated head shaking. One of these which consumed 11.8 grams vomited. A later test 5 with five pigeons gave similar results, with one vomiting and two retching although less feed was consumed.

Gitoxigenin Results

In test 4, six pigeons with an average weight of 632 grams were offered 0.03% gitoxigenin treated cracked corn diets. The six pigeons consumed an average of 3.9 grams of treated feed averaging 1.83 mg/kg of gitoxigenin per bird. Three of the pigeons demonstrated a little head movement but the other three showed no effects. There was no retching or vomiting although one pigeon consumed 9.4 grams of the treated feed.

Oleandrigenin Results

In test 2, six pigeons with an average weight of 641 grams were offered 0.03% oleandrigenin treated cracked corn diets. The six pigeons consumed an average of 3.07 grams of treated feed averaging 1.61 mg/kg of oleandrigenin per bird. Three pigeons retched and vomited within 13-22 min., two pigeons within 90-150 minutes, and one pigeon consuming only 0.70 mg/kg did not even retch.

Oleandrin Results

Oleandrin was tested in eight pigeon systems at dose levels of 0.03%, 0.01% and 0.005%.

Tests 3 and 6 were carried out on 0.03% oleandrin treated corn. in test 3 six pigeons with an average weight of 598 grams ingested an average of 2.94 mg/kg oleandrin per bird. All of the pigeons retched and vomited within 12-36 min. In test 6 six pigeons with an average weight of 630 grams ingested an average of 0.97 mg/kg of oleandrin per bird. Four that consumed little or no treated diet showed no reaction whereas two retched and vomited within 14 min. and 18 min.

In test 7 six pigeons with and average weight of 651 grams ingested 0.01% oleandrin treated corn, averaging 0.28 mg/kg oleandrin per bird. Three of the pigeons consumed nothing or virtually nothing and did not react. Three retched within 10 min. of first feeding, then vomited later. In test 0.01% oleandrin treated corn was offered to a total of 6 naive pigeons. retched within 10-20 min., and five vomited 1-3 min. later. These pigeons participated in a later test 14.

In test 14 three pigeons from test 12 were offered 0.01% oleandrin treated cracked corn 28 days after their first exposure to this bait. Although consumption was very low two of the three pigeons did retch and vomit. A third pigeon retched several times before even testing the corn. Following the 1 hr. test, these three pigeons were each given a bowl of untreated cracked corn and left for an additional 1.5 hrs in the test cages. The consumption of clean cracked corn was 0.0, 0.1 and 0.5 g respectively indicating a rejection of this untreated cracked corn also. These pigeons demonstrated a strong learned aversion to untreated cracked corn.

In test 13 0.005% oleandrin treated corn was offered to three pigeons. All retched within 18-30 min., then vomited within 28-45 min. Although the calculated average 1.02 mg/kg oleandrin ingested is relatively large, this is misleading as most of the contaminated corn was eliminated through vomiting. Hence, only that oleandrin which could be absorbed prior to vomiting was responsible for the physiological reactions. These same pigeons, naive here, participated in a later test 15.

In test 15 0.005% oleandrin treated cracked corn was offered to three pigeons from test 13 some 22 days later. None of these pigeons ate any bait, not even tasting it. This rejection was based on vision alone, as demonstrated in test 14 where untreated cracked corn was rejected by tribal pigeons. Two of tile three pigeons actually retched immediately after the bowl of treated corn was put in the cage.

In test 16 three pigeons from tests 13 and 15 were offered 0.005% oleandrin treated cracked corn 77 days and 99 days after initial exposure to oleandrin-treated cracked corn. Two of the three pigeons retched even before tasting the corn and one vomited. The diet bait consumed by these three pigeons was 0.1 g, 0.1 g and 0.2 g respectively, averaging 0.01 mg/kg oleandrin per bird. Following the 1 hour test plus a one hour waiting period, each pigeon was offered a bowl of untreated cracked corn and a bowl of pigeon mix. Less than 0.1 gram of the clean cracked corn was consumed by each bird, but the pigeon mix was consumed in relatively substantial amounts of 25.1 grams, 14.6 grams and 32.6 grams respectively over a 1 hour feeding period. This clearly indicates a learned aversion to cracked corn.

Oleander Extract Results

In test 9 an oleander extract on cracked corn amounting to 0.015% oleandrin was offered to six pigeons with an average weight of 698 grams. Three pigeons ate little or no grain and were unaffected. One pigeon ingested 0.1 gram of bait containing 0.023 mg/kg oleandrin and retched. One bird ingesting 0.25 mg/kg oleandrin on 1.2 grams of bait did not retch or vomit. The sixth pigeon ingested 4.9 grams of bait containing 0.97 mg/kg oleandrin, then retched anti vomited in about 30 minutes. Some of these pigeons, taken from a common cage, had apparently been used in prior tests, and had learned to avoid cracked corn.

In test 10 an oleander extract on cracked corn amounting to 0.02% oleandrin was offered to three pigeons with an average weight of 529 grams. These birds were deprived of food for 24 hours prior to testing rather than the standard 48 hours, and were apparently not hungry enough to feed to any extent. Since these birds were fresh and naive, their lack of bait consumption was apparently due to taste or odor of the extract which contained about 50% products other than oleandrin. Two birds ate 0.1 gram and 0.2 gram of the bait respectively and did not react. The third bird consumed 1.2 grams of bait amounting to a 0.4 mg/kg dose of oleandrin, then vomited in the second hour of the test period.

In test 11 an oleander extract on cracked corn amounting 0.02% oleandrin was offered to six pigeons with an average weight of 590 grams, who had fasted for the normal 48 hours. The six birds consumed an average of 8.78 grams amounting to 3.03 mg/kg oleandrin per bird, but regurgitated an average of 7.55 grams of dry vomitus. Five of the six birds retched within 10-30 minutes into the test, and vomited later. One bird that consumed 9.3 grams of bait exhibited a lot of head shaking but did not retch and vomit until the second hour of the test period. The retching and vomiting was strong in all of these naive pigeons. A typical summary of this test is demonstrated in Table 3.

Scillirosidin Results

In test 17 three pigeons with an average weight of 293 grams were offered a 0.01% scillirosidin treated cracked corn feed. Two of the three pigeons retched and vomited after 15 and 80 minutes having eaten 0.4 and 0.7 grams respectively. The third pigeon ate only 0.1 gram and did not react.

In test 18 three pigeons with an average weight of 371 grams were offered a 0.03% scillirosidin treated cracked corn feed. All three pigeons reacted strongly, vomiting within 7-9 minutes after feeding.

In test 19 the same six pigeons who had been offered 0.01% and 0.03% scillirosidin in their feed were again tested 8 and 13 days later on a 0.05% scillirosidin treated cracked corn. This time only two of the pigeons ate enough to show a strong emetic action, both within 0-13 minutes of feeding. The other four picked at tile feed, eating little and regurgitation only mildly several times, with initial emesis effects observed at 1, 19, 102 and 180 minutes. The hesitancy by most of these pigeons to eat the 0.05% scillirosidin treated feed was apparently due to their previous experience with scillirosidin treated corn. No mortality occurred in any of the pigeons.

EXAMPLE 8

Rodent Testing

Test Method

Rodent baits were prepared on course cracked corn or a standard EPA-type diet by soaking the grains with an alcohol solution of the emetic product, mixing it well, then allowing it to dry thoroughly in an open tray overnight. Some baits were ground or rolled to alter absorption qualities of the alcohol. The dried baits were stored at room temperature for as long as four weeks. The EPA-type diet consists of ground corn (65%), ground oat groats (25%), food grade corn oil (5%) and food grade powdered sugar (5%).

The rodents in the test groups were sexed, weighed and individually caged and acclimated to the laboratory for a minimum of seven days. Water and maintenance diets were provided ad lib. On the day of the test, maintenance diet was removed in the morning and the animals deprived of until the test was set up in the late afternoon. A weighed amount of test diet was given to each animal of the test group. In the no-choice tests, one bowl of diet was provided. In free-choice tests, two bowls were provided, one with the standard diet and one with the treated diet. The feed bowls were removed the next day about twenty hours after they were offered. The amount of diet remaining was weighed including any spillage. Following this test, the rodents were again given their maintenance diet and kept under observation for seven days.

Oleandrin And Wild House Mice—Test 20

Five wild house mice, two males and three females, were provided with a no-choice diet of 0.03% oleandrin on course cracked corn. The mean 20 hour consumption was 0.38 grams, which resulted in a mean of 5.6 mg/kg oleandrin intake for these 20.2 gram(mean) mice. The average intake of oleandrin per mouse was 0.11 mg.

No mortality occurred. Consumption of the bait was low, indicating poor acceptance.

Oleandrin And Laboratory Mice—Test 21

Ten Swiss Webster laboratory mice, sexes equal, were provided with a no-choice 0.3%, oleandrin treated EPA-type diet in a 20 hour test. Diet consumption was low with a mean of 0.12 grams, and a mean oleandrin intake of 14.5 mg/kg for these 25.0 gram,(mean) mice. One mouse, a male, died after consuming 49.6 mg/kg oleandrin, which was four times the average. A control group of ten Swiss Webster mice consumed an average of 5.9 grams each. Therefore, the mice offered the oleandrin treated diet consumed only 2.0% of the diet eaten by the controls.

Oleandrin And Laboratory Rats—Test 22

Six Sprague-Dawley laboratory rats, sexes equal, were provided with a no-choice 0.3% oleandrin treated EPA-type diet in a 20 hour test. The mean diet consumption was 2.1 grams, and the mean oleandrin intake was 35.4 mg/kg for these 173.1 gram (mean) rats. No deaths occurred. Consumption for females was about half that for males. A control group of six Sprague-Dawley rats consumed an average of 14.8 grams each. Therefore, the rats offered the oleandrin treated diet consumed only 14.2% of the standard untreated EPA-type diet eaten by the controls.

Oleander Extract And Rats—Free Choice—Test 23

Six Sprague-Dawley rats, equal sexes, were provided with a free-choice of diets for 1 day. One diet was the standard EPA-type, and the second diet was treated with an oleander extract product at 0.02% oleandrin on the grain. Consumption of the placebo diet averaged 9.3 grams per rat, compared to 6.3 grams for the treated diet. The average oleandrin consumed was 7.4 mg/kg. There was a 60/40 preference toward the untreated diet over tile treated diet. Total consumption of both diets was 5.6 grams (mean) compared to 14.8 grams (mean) for six contros. No deaths occurred.

Scillirosidin and Laboratory Rats

A scillirosidin preparation containing 67% active product was tested in five Sprague-Dawley rat systems at dose levels of 0.01, 0.03 and 0.05%. In each test the basic EPA-type diet was treated with an alcohol solution of the scillirosidin product. The animals were exposed to the treated diets for one day, then monitored for mortality for at least seven days longer. Each test included three males and three females. Results are in Table 2., tests 24–28.

At a 0.01 level, tests 24 and 25, there were no deaths indicating that both male and female rats learned to avoid the bait before ingesting a lethal dose, consuming an average of only 1.4 and 2.4 grams of baits. These rats normally consume about 15 grams of feed during a one day period.

At a 0.03 level, tests 26 and 27, the rats still only consumed 1.4 and 1.3 grams of bait, but the dose of scillirosidin was higher. Accordingly, all six of the female rats died in these two tests, the females being more susceptible to scillirosidin toxicity than males. A lethal dose of scillirosidin for six female Sprague-Dawley rats ranged from 1.46 to 2.25 mg/kg of scillirosidin ingested, averaging 1.83 mg/kg.

At a 0.05% scillirosidin level in the feed, test 28, two of the three females died, one ingesting 1.39 mg/kg scillirosidin and the second 4.93 mg/kg. One female ingested 1.48 mg/kg and lived through the 8 day test period. None of tile three males averaging 2.95 mg/kg of ingested scillirosidin died.

EXAMPLE 9

Pocket Gophers—Test 29

Six pocket gophers, *Thomomys bottae*, average weight 121.1 grams, were offered a crimped oat groat dish prepared with an oleandrin level of 0.3% in a one-day no-choice test. The mean diet consumption was 0.83 grams, which was 12% of a placebo diet consumed the day before. The oleandrin intake ranged from 12.4 to 30.1 mg/kg, for a mean of 20.6 mg/kg. All six gophers showed severe signs of toxicosis and three died. Pocket gophers seemed more susceptible to oleandrin toxicosis than any other rodent tested.

EXAMPLE 10

Meadow Voles—Test 30

Six meadow voles, *Microtus californicus*, average weight 57.3 grams, were offered a crimped oat groat diet prepared with an oleandrin level of 0.3% in a one-day no-choice test. The mean diet consumption was 0.72 grams, which was 16% of a placebo diet consumed the day before. The oleandrin intake ranged from 17.5 to 58.9 mg/kg for a mean of 38.9 mg/kg. There were no deaths. The low consumption of test diet is apparently due to the sickness caused by oleandrin, resulting in an aversion to the feed.

References Cited

1. Belt, E., Red Squill and Rat Control, Proc. Cong. Drugs Assoc. Econ. Plants, Los Angeles, 61–66(1944).
2. Black, H. C., Ed., Silviculture Approaches to Animal Damage Management in Pacific Northwest Forests, USDA Forest Service General Technical Report, PNW-GTR-287, 442 pp, (January 1992).
3. Brower, L. P. and L. S. Fink, A Natural Toxic Defense System: Cardenolides in Butterflies Versus Birds, Ann. N.Y. Acad. Sci., 443:171–187(1985), in Experimental Assessments and Clinical Applications of Conditioned Food Aversions, ,N. S. Braveman and P. Bronstein, Eds.
4. Campbell, D. L., J. P. Farley and L. E. Johnson, Draft Report of Conditioned Aversion of Mountain Beavers to Oleandrin Extract, Denver Wildlife Research Center, USDA, Olympia, Washington (Feb. 25, 1991).
5. Conover, M. R., Potential Compounds for Establishing Conditioned Food Aversions in Raccoons, Wildl. Soc. Bull., 17:430–435(1989).
6. Gaafar, S. M., W. E. Howard and R. E. March, Eds., Parasites, Pests and Predators, 575 pp., Elsevier Science Publ., Amsterdam, (1985).
7. Gold, H., M. Cattell, W. Modell, T. Greiner and R. Guevara, Local Emetic Activity of Glycosides of the Digitalis Series, J. Pharmacol. Exptl. Therap., 98:337–345(1950).
8. Marsh, R. E., Vertebrate Pest Management, pp. 253–285, from Adv. Urban Pest Mgmt., G. W. Bennett and J. M. Owens, Eds., Van Nostrand Reinhold, N.Y. (1986).
9. Marsh, R. E., Rodent Problems on the North American Continent, pp. 1–11, from Rodent Pest Management, I. Prakash, Ed., CRC Press, Boca Raton, Fla. (1988).
10. Marsh, R. E. And W. E. Howard, Vertebrate Pests, pp. 771–834, from Handbook of Pest Control, A. Mallis, Ed., Franzak and Foster Co., Cleveland, Ohio (1990).
11. Marsh, R. E., W. E. Howard, A. D. Tunberg and A. J. Verbiscar, Preliminary Report of the Laboratory Efficacy of Scillirosidin and Scillireside, Wildlife and Fisheries Biology, Univ. Calif., Davis and Anver Bioscience Design, (Dec. 20, 1985).
12. Marsh, R. E. and A. J. Verbiscar, Preliminary Report of A Laboratory Bioassay Study of Emetic Compounds From Plant Sources as Possible Rodenticides or Pesticide Additives, Wildlife and Fisheries Biology, Univ. Calif., Davis, and Anver Bioscience Design (Jan. 20, 1991).
13. Nachman, M. and P. L. Hartley, Role of Illness in Producing Learned Taste Aversions in Rats, J. Comp. and Physiol. Psychology, 89:1010–1016(1975).
14. Riley, A. L. and D. L. Tuck, Conditioned Taste Aversions: A Behavioral Index of Toxicity, Ann. N.Y. Acad. Sci., 443:271–292(1985), N. S. Braveman and P. Bronstein, Eds.
15. Rothlin, E. and W. R. Schalch, Zur Pharmakologie and Toxikologie des Scillirosids und des Scillirosidins, Helv. Physiol. Acta, 10:427–437(1952).
16. Schafer, E. W., W. A. Bowies and J. Hurlbut, The Acute Oral Toxicity, Repellency and Hazard Potential of 998 Chemicals to One or More Species of Wild and Domestic Birds, Arch. Environm. Contam. Toxicol., 12:355–382(1983).
17. Schwartz, W. L., W. W. Bay, J. W. Dolahite, R. W. Storts and L. H. Russell, Toxicity of *Nerium oleander* in the Monkey, Vet. Path., 11: 259–277(1974).
18. Secoy, D. M. and A. E. Smith, Use of Plants in Control of Agricultural and Domestic Pests, Econ. Bot., 37:28–57(1983).
19. Shaw, D. and J. Pern, Oleander Poisoning, Med. J. Aust., 2:267–269(1979).
20. Szabuniewicz, M., J. D. McCrady and B. J. Camp, Treatment of Experimentally Induced Oleander Poisoning, Arch. Int. Pharmacodyn., 189:12–21 (1971).
21. Verbiscar, A. J., T. F. Banigan and R. A. Schatz, Modification of Red Squill by *Aspergillus niger*, J. Agric. Food Chem., 35:365–368(1987).
22. Verbiscar, A. J., J. Patel, T. F. Banigan and R. A. Schatz, Scilliroside and Other Compounds in Red Squill, J. Agric. Food Chem., 34:973–979(1986).
23. Wang, S. C., Emetic and Antiemetic Drugs, Physiol. Pharmacol., 2:255–328(1965).

What is claimed is:

1. A method for repelling wildlife using products from *Nerium oleander* and *Urginea maritima* which after application by spraying, brushing or dipping, with solutions or suspensions, on plant, animal or other targets susceptible to damage by animals or birds, cause nausea or emesis when ingested.

2. A method of claim 1 where the active product is dissolved in a low boiling alcohol solvent including methanol, ethanol or isopropanol for application to targets.

3. A method of claim 1 where the active product is suspended in an aqueous system with an acidity range of pH 4.5 to pH 7.5, containing methylcellulose, ethylcellulose, hydroxyethylcellulose, hydroxypropylcellulose or other polymer as a non-hydrolytic binder for the products to the targets.

4. A method of claim 1 where nausea and emesis occur at a dose lower than a lethal dose when the active product applied to a target is ingested by animals or birds.

5. A method of claim 1 where aversion conditioning occurs wherein the animals or birds remember the repellent experience.

6. A method of claim 1 where the active product is oleandrin.

7. A method of claim 1 where the active product is oleandrigenin.

8. A method of claim 1 where the active product is scillirosidin.

9. A method of claim 1 where the active product is an extract of bulbs, leaves, twigs, stems, flowers or ariel parts combined.

10. A method of claim 1, where the active product is dried whole powdered bulbs, leaves, twigs, stems, flowers or ariel parts combined.

* * * * *